United States Patent [19]

Niznick

[11] Patent Number: 5,622,500
[45] Date of Patent: Apr. 22, 1997

[54] INSERTION TOOL/HEALING COLLAR/ABUTMENT

[75] Inventor: Gerald A. Niznick, Las Vegas, Nev.

[73] Assignee: Core-Vent Corporation, Las Vegas, Nev.

[21] Appl. No.: 201,534

[22] Filed: Feb. 24, 1994

[51] Int. Cl.$^6$ ......................................................... A61C 8/00
[52] U.S. Cl. ............................................ 433/173; 206/63.5
[58] Field of Search ..................................... 433/173, 174, 433/175, 176; 206/368, 369, 438, 63.5

[56] References Cited

U.S. PATENT DOCUMENTS

| | | | |
|---|---|---|---|
| 4,856,648 | 8/1989 | Krueger | 206/63.5 |
| 4,856,994 | 8/1989 | Lazzara et al. | 433/174 |
| 5,062,800 | 11/1991 | Niznick | 433/173 |
| 5,076,788 | 12/1991 | Niznick | 433/173 |
| 5,108,288 | 4/1992 | Perry | 433/173 |
| 5,297,963 | 3/1994 | Dafatry | 433/173 |
| 5,316,476 | 5/1994 | Krauser | 433/173 |
| 5,322,443 | 6/1994 | Beaty et al. | 433/173 |
| 5,336,090 | 8/1994 | Wilson, Jr. et al. | 433/173 |
| 5,338,196 | 8/1994 | Beaty et al. | 433/173 |
| 5,368,160 | 11/1994 | Leuschen et al. | 433/174 |

Primary Examiner—Cary E. O'Connor

[57] ABSTRACT

A healing collar for use with an endosseous dental implant that has an internal-threaded passage and at the top has a multi-sided male projection includes a cylindrical-shaped external surface, a first cavity at one end that has the same number of sides as the male projection atop the implant and a size and shape adapted to fit frictionally or non-frictionally over the male projection. At the other end of the healing collar is an opening leading to a second internal cavity having a plurality of sides adapted to engage a tool suitable for inserting an implant, joined to the healing collar, into a passage formed in the jawbone of a patient formed to receive the implant. Between the first and second internal cavities is an inwardly-projecting flange that has upper and lower annular surfaces for engaging the head a fixation screw, and the top surface of the implant, respectively.

15 Claims, 9 Drawing Sheets

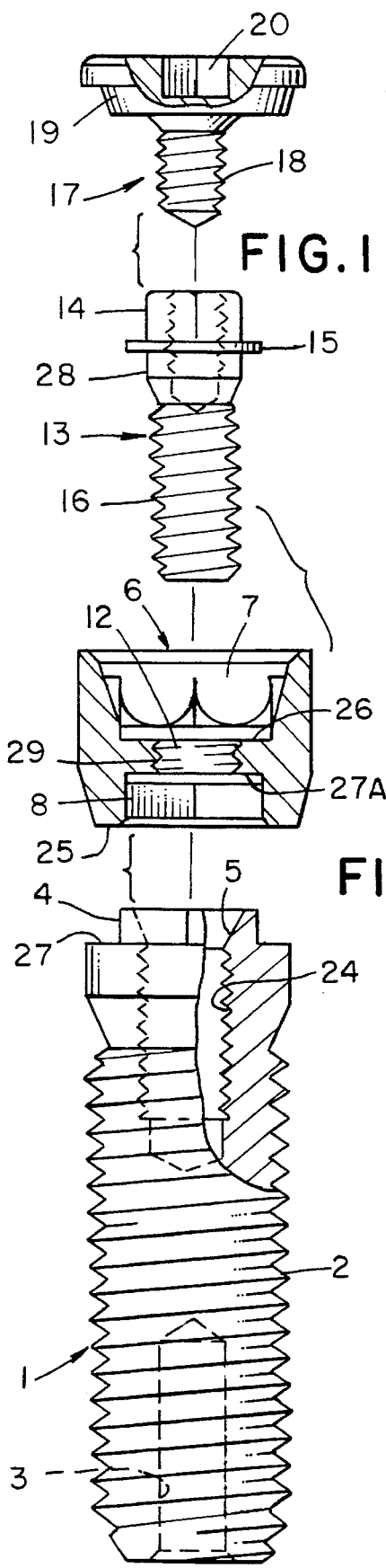
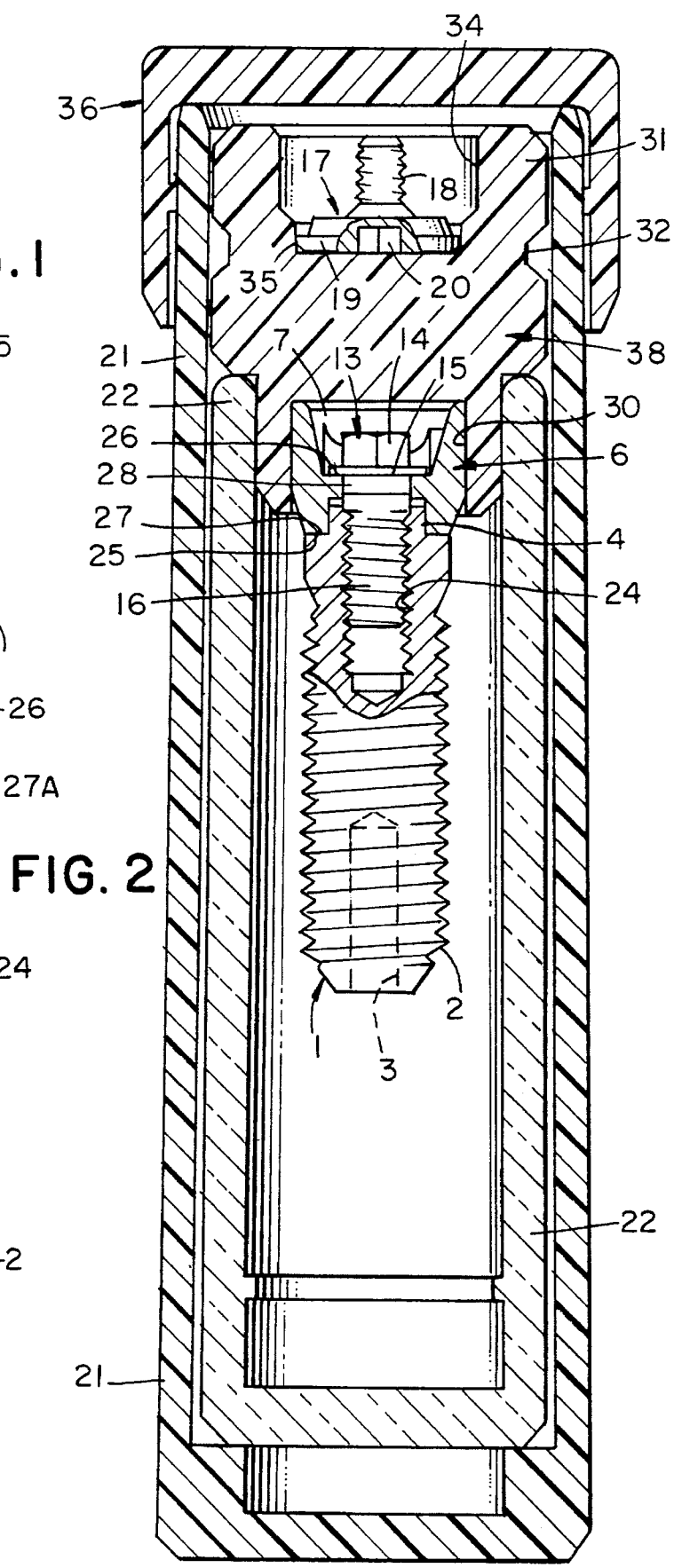

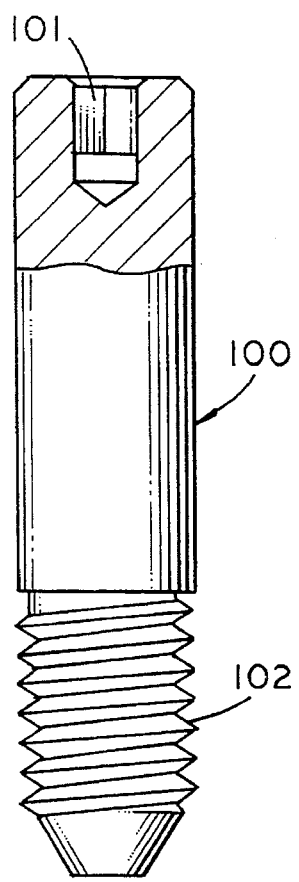
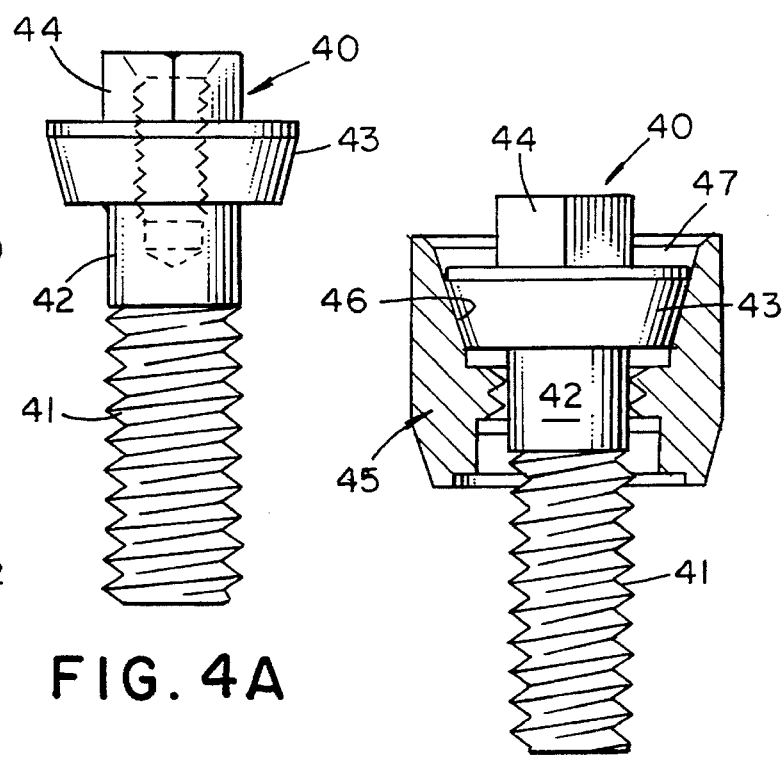
FIG. 3
FIG. 4A
FIG. 4B
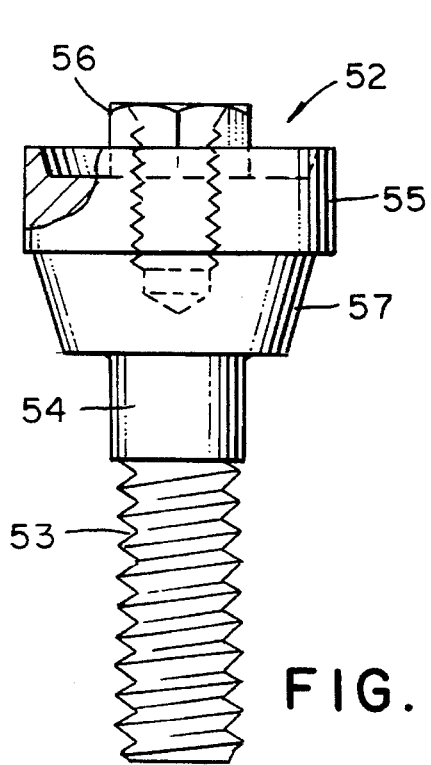
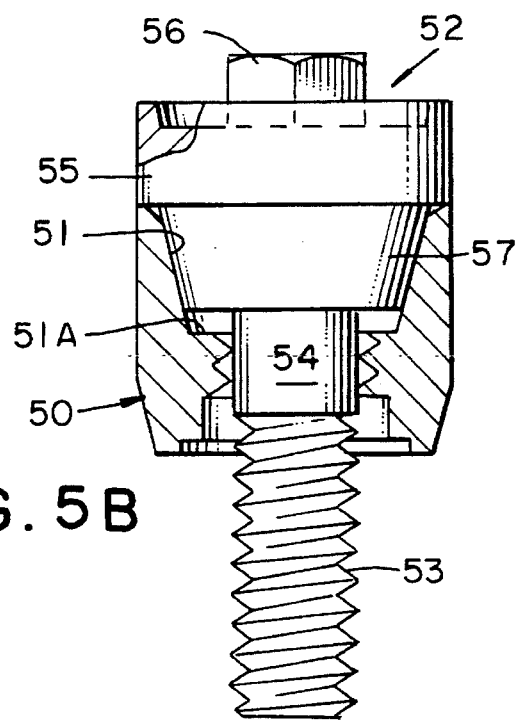
FIG. 5A
FIG. 5B

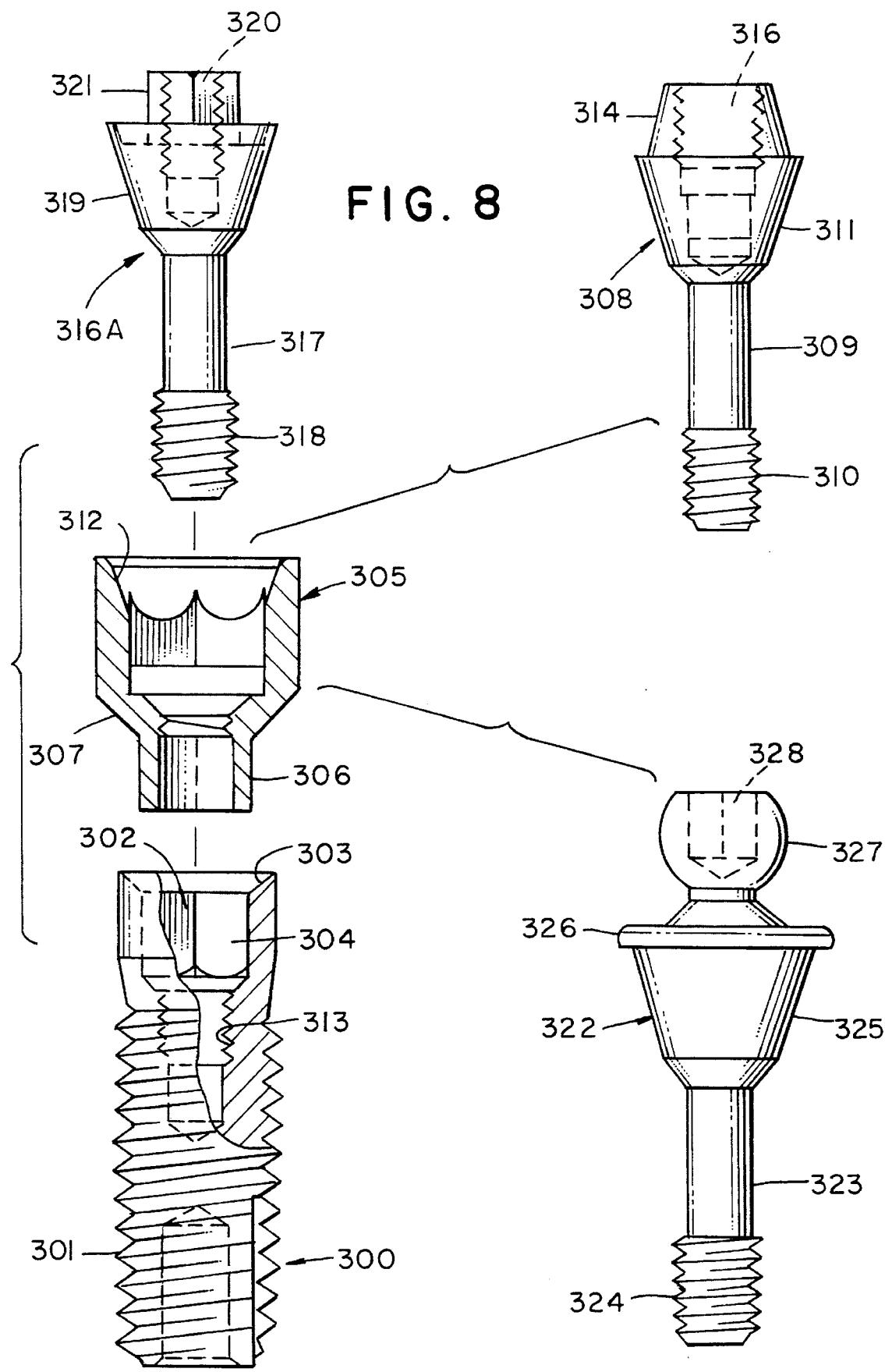

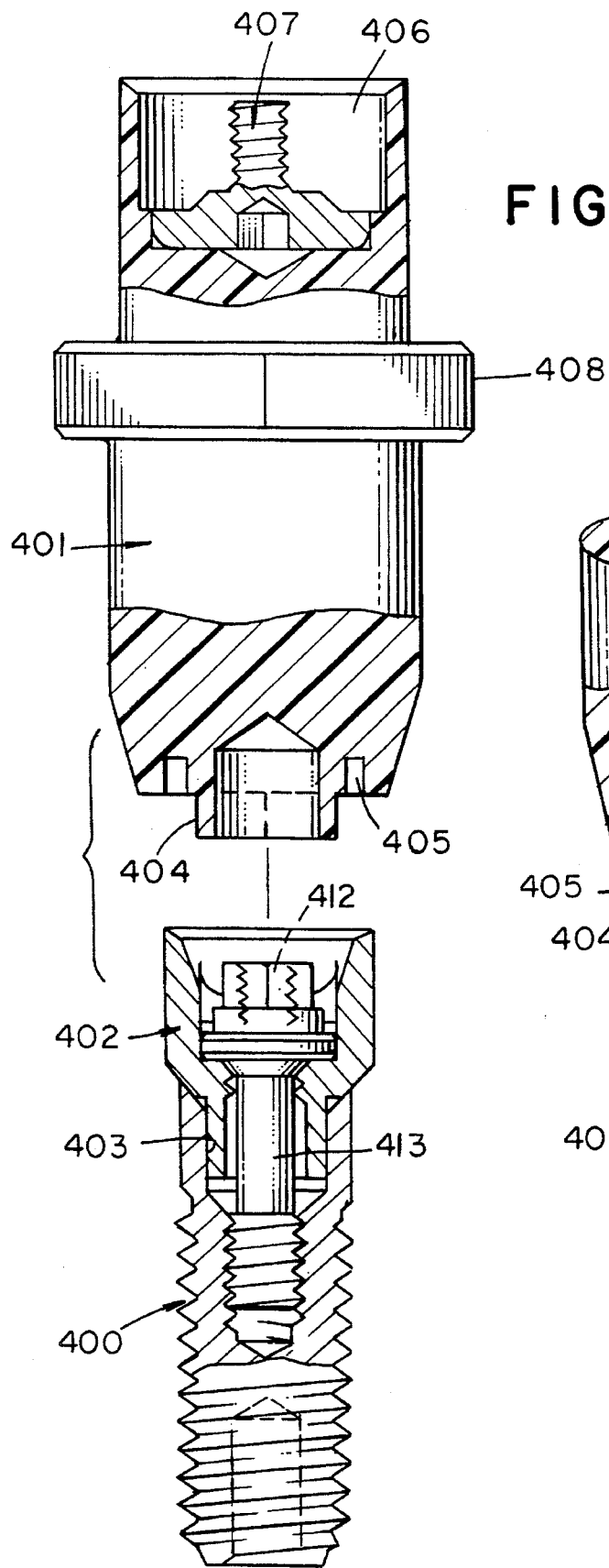
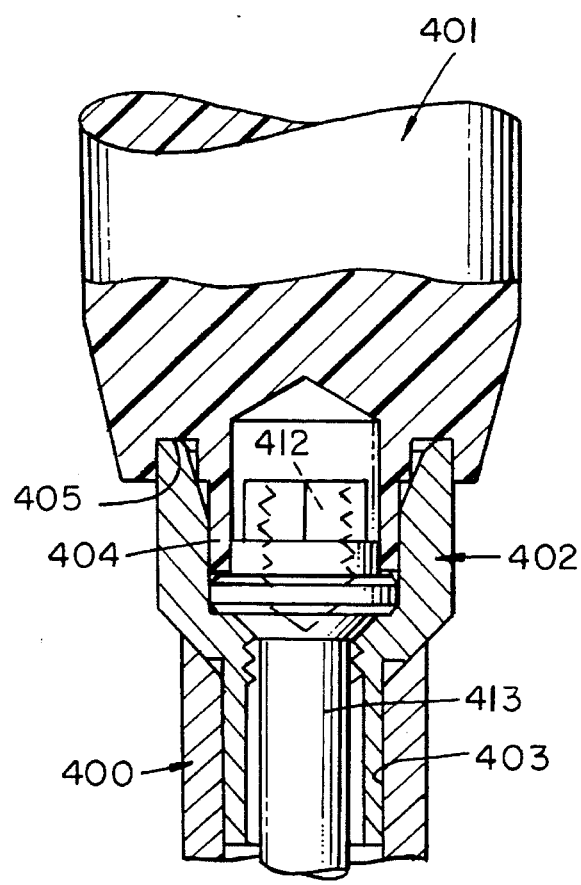
FIG. 9A
FIG. 9E

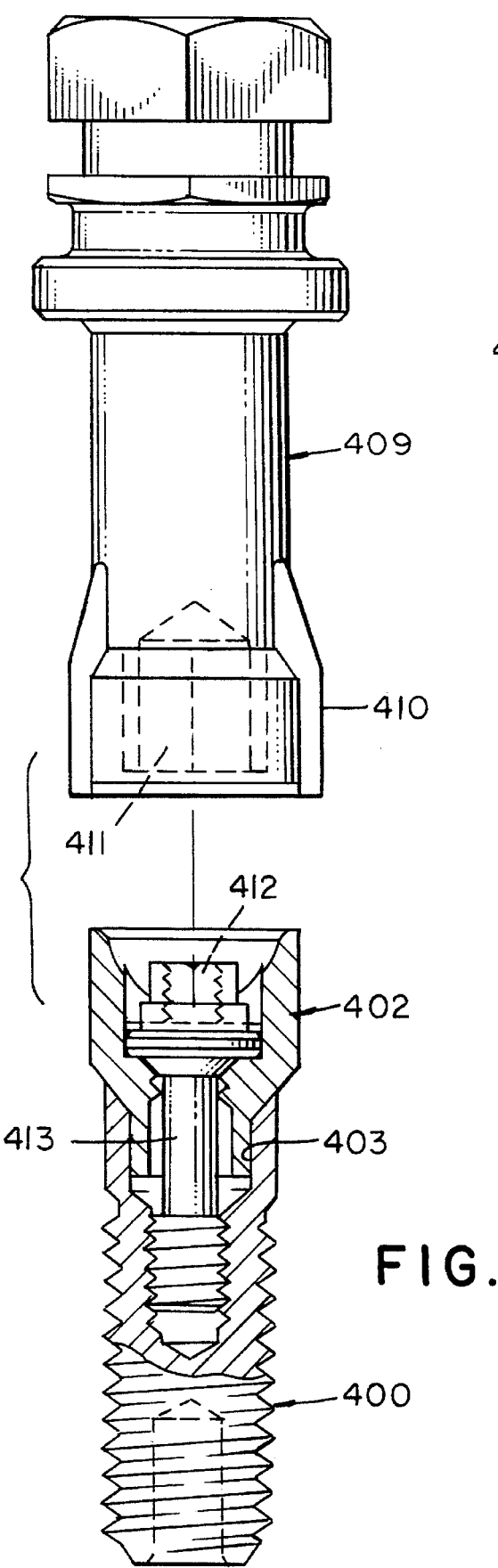
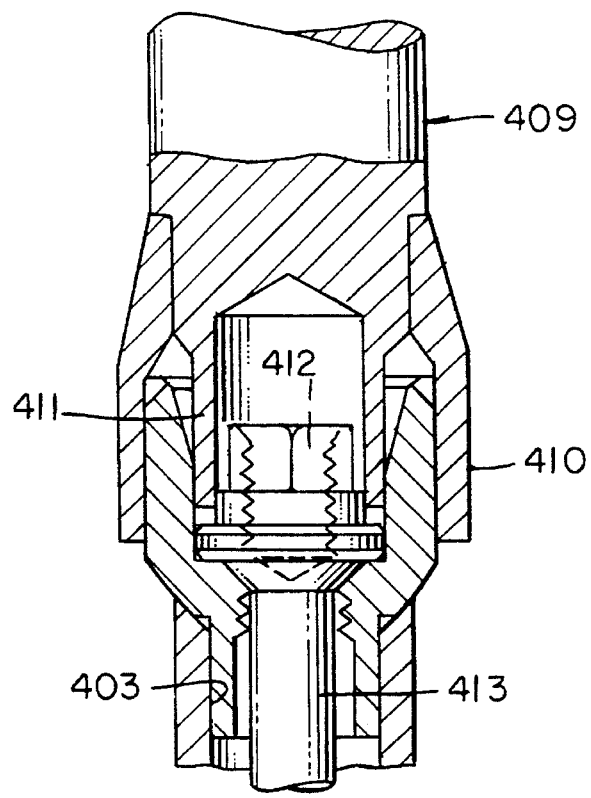
FIG. 9F
FIG. 9B

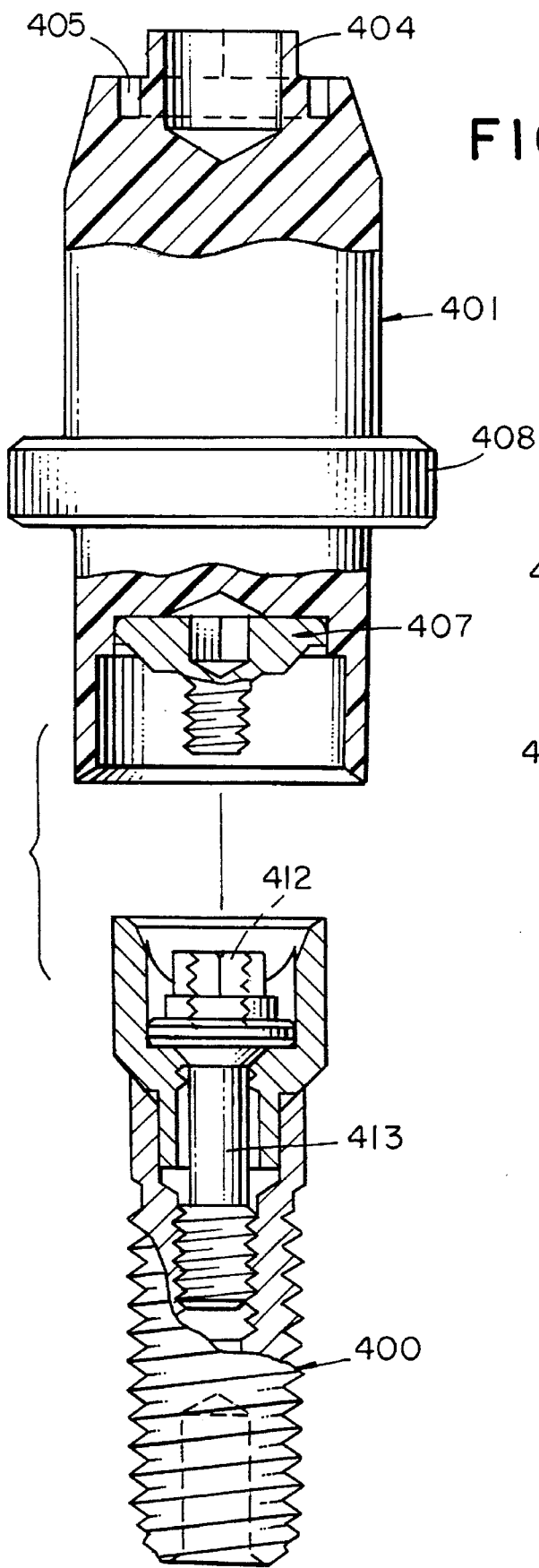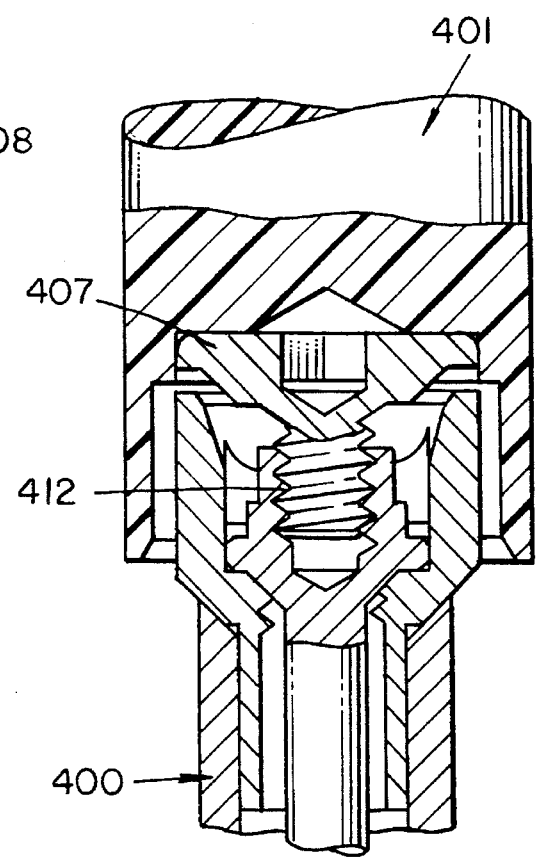
FIG. 9C
FIG. 9G

INSERTION TOOL/HEALING COLLAR/ABUTMENT

BACKGROUND OF THE INVENTION

This invention relates to a healing collar for use with endosseous dental implants. This healing collar can also serve as an insertion tool, and, in some embodiments, as part of an abutment. In the preferred embodiments, this healing collar includes two parts, a hollow collar member and a fixation screw member. The fixation screw member has a size and shape that allows the screw to pass into one end of the collar member, through the collar member, and into an internal, threaded passage inside the body of an endosseous dental implant upon which the healing collar placed. Inside the healing collar is an inwardly-projecting, annular flange or shelf to engage the bottom surface of the head on the screw member. In some embodiments, this flange or shelf is part of an annular projection that is threaded on its inner edge. These threads cooperate with a threaded tool to disengage the collar from the top of an implant, and is especially useful where the collar/implant interface is a snug, frictional connection.

This invention also relates to an implant package that includes a frictionally-fitting stopper for an endosseous implant container. At one end of the stopper is a first internal cavity for receiving and engaging frictionally the outer surface of the healing collar, and/or for engaging the internal, multi-sided internal cavity in the healing collar. In the package, the healing collar is connected to an endosseous dental implant by the fixation screw member, but can also be connected to the implant, alternatively, by frictional fit. In preferred embodiments, the other end of this stopper comprises a second internal cavity having a size and shape appropriate to receive a healing screw that frictionally engages the walls of the internal passage. This stopper allows an endosseous dental implant to be carried to a surgical site and to be initially inserted into the site without touching the surface of the implant. Following full seating of the implant into the site, by threading if a screw implant, or by tapping if a cylindrical implant, the stopper then serves as an insertion tool for the healing screw.

Alternative embodiments of this stopper receive and engage frictionally the outer surface or inner surface of a dental implant in the first internal cavity and the head of a fixation screw in the second internal cavity at the other end of the stopper.

The healing collar, in preferred embodiments, has a generally cylindrical exterior shape and is open at both ends. At a first end, the healing collar has a multi-sided internal cavity that is configured to fit over the top of an endosseous dental implant having at the top a multi-sided projection of complementary size and shape as in Core-Vent Corporation's SWEDE-VENT implant. Alternatively, the collar has a multi-sided projection at the first end that fits into an internal, multi-sided passage at the top of the implant, as in Core-Vent Corporation's SCREW-VENT (externally-threaded) and BIO-VENT (externally-unthreaded cylinder) brand implants.

At the second end of the healing collar is an internal, multi-sided surface that may receive and engage a multi-sided tool of complementary size and shape. This multi-sided surface may, for example, form a six-sided figure. In preferred embodiments, an internal, beveled or tapered surface lies above the internal multi-sided surface. This beveled or tapered region preferably has a degree of taper, with respect to the longitudinal axis of the sidewall of the implant, of about 12 degrees to about 18 degrees, but preferably about 15 degrees. This beveled or tapered region has a length sufficient to receive and engage a complementary, tapered portion of an abutment screw that has a tapered head portion that seats in the tapered, internal portion of the cavity at the second and of the healing collar.

The inwardly-projecting flange or shelf internal to, and between the first and second ends of the healing collar is of a size and shape to engage the head of a fixation screw member on one surface and, on the other surface, is of a size and shape appropriate for seating upon the top of an endosseous dental implant. Between these two surfaces, the flange preferably includes a threaded region for engaging a threaded shank on a screw or a tool designed to disengage the healing collar from the top of the implant if they frictionally fit together. The head of the fixation screw is preferably multi-sided. The space between this head and the internal multi-sided wall of the healing collar is sufficiently large to permit insertion of a multi-sided tool of complementary size and shape into the space to turn an implant connected to the healing collar into a passage in the jawbone of a patient. The outer wall of the healing collar is preferably cylindrical.

The fixation screw member, in preferred embodiments, has a head member that is multi-sided and of sufficiently small cross-sectional dimensions that a tool can fit over the head of the screw member, and can engage the multi-sided, internal walls of the healing collar. The head of the fixation screw may also have a slotted top or external or internal wrench-engaging surfaces and, in a preferred embodiment, an internal thread for receiving the threaded shank of a cover screw.

In preferred embodiments, the shank of a cover screw passes through the internal passage of the healing collar and screws into an internal passage in the body of the implant, or screws into internal threads in the head of a fixation screw member.

Preferred embodiments of the healing collar also can receive, and interfit with, a wide variety of abutment screws. One embodiment of such an abutment screw engages internal threads in a fixation screw member. Another embodiment engages internal threads inside the body of an endosseous dental implant, thus affixing the healing collar to the top of the implant. With these embodiments, the healing collar becomes part of the abutment. The abutment screw may have a straight or tapered upper end to receive a dental prosthesis, and, in some cases, an internally-threaded passage near the top to accept another screw that retains a dental prosthesis. The outer surface of the upper end may be multi-sided to allow engagement of a wrench or other tool, or may include an internal, multi-sided surface formed above, below or in the internal threads to receive a fastener to retain a dental prosthesis. Alternatively, the abutment screw can include a ball member for connection to a snap retainer in a dental prosthesis or a tapered solid member for attachment, as by cementation, of a dental crown or bridge.

The healing collar of this invention, in cooperation with a fixation screw member, a cover screw and/or an abutment screw, can engage a dental implant frictionally or non-frictionally. Frictional engagement results where the implant has a multi-sided projection at the top with a plurality of tapered sides, as disclosed in U.S. patent application No. 08/099,070, filed in the U.S. Patent & Trademark Office on Jul. 28, 1993. Alternatively, the healing collar may have a multi-sided projection that fits into an internal, multi-sided passage inside a dental implant where a plurality of the sides of the projection are tapered. See, for example, the tapered projection on the abutments disclosed in U.S. patent application No. 07/909,119 filed Jul. 6, 1992. Upon attachment to the top of the implant, the healing collar can function as an implant insertion tool alone, or as an insertion tool and a healing collar, if the collar is left in a patient's mouth immediately after insertion of the implant. In the latter case, the healing collar atop the implant is transmucosal, holding open the mucosal tissue above the implant during the healing period. This surgical protocol is commonly called "non-submerged healing" or "one-stage surgery".

The healing collar, when left atop a dental implant, can also function as part of an abutment. An abutment screw that interfits with the healing collar completes such an abutment. The healing collar may also function as an abutment collar even if the healing collar is detached from an implant promptly after insertion of the implant into a patient's mouth to allow submerged healing with the tissue covering the implant. The healing collar can be re-attached after a 3–6 month healing period, and used both for keeping mucosal tissue open during healing after the second surgery and/or as the collar of a 2-piece abutment.

Thus, the new healing collar provides many different functions: an implant insertion tool alone, a healing collar alone, an abutment part alone, an insertion tool/healing collar, an insertion tool/healing collar/abutment part, an insertion tool/abutment part, and a healing collar/abutment part. This collar can be configured to fit over implants that have external, multi-sided projections, or implants that have internal, multi-sided passages, and can be retained by a fixation screw for non-friction fit healing collars. These collars can also be configured to fit frictionally over implants that have tapered, multi-sided projections, or to engage internal implant passages frictionally with tapered projections on the collar itself.

BRIEF DESCRIPTION OF THE DRAWINGS

The new healing collars of this invention can better be understood by reference to the drawings, in which:

FIG. 1 shows one embodiment of the healing collar, here configured to fit over the top of an endosseous dental implant having an external multi-sided projection and an internally-threaded passage, and embodiments of a fixation screw member and a cover screw for use with this healing collar;

FIG. 2 shows one embodiment of a healing collar/dental implant package that includes a package stopper configured to carry an endosseous implant/healing collar/fixation screw member combination to the jawbone of a patient;

FIG. 3 shows an embodiment of a removal tool for detaching a friction-fitted healing collar embodiment from a dental implant;

FIGS. 4A and 4B show a second embodiment of a healing collar/fixation screw member;

FIGS. 5A and 5B show a third embodiment of a healing collar/fixation screw member;

FIG. 8 shows one embodiment of the new healing collar with a beveled or tapered internal wall portion above the multi-sided wall portion at the top of the healing collar that receives and engages a plurality of abutment screws having tapered head portions that seat in this internal, tapered region.

DETAILED DESCRIPTION OF THE DRAWINGS

Figure 6:
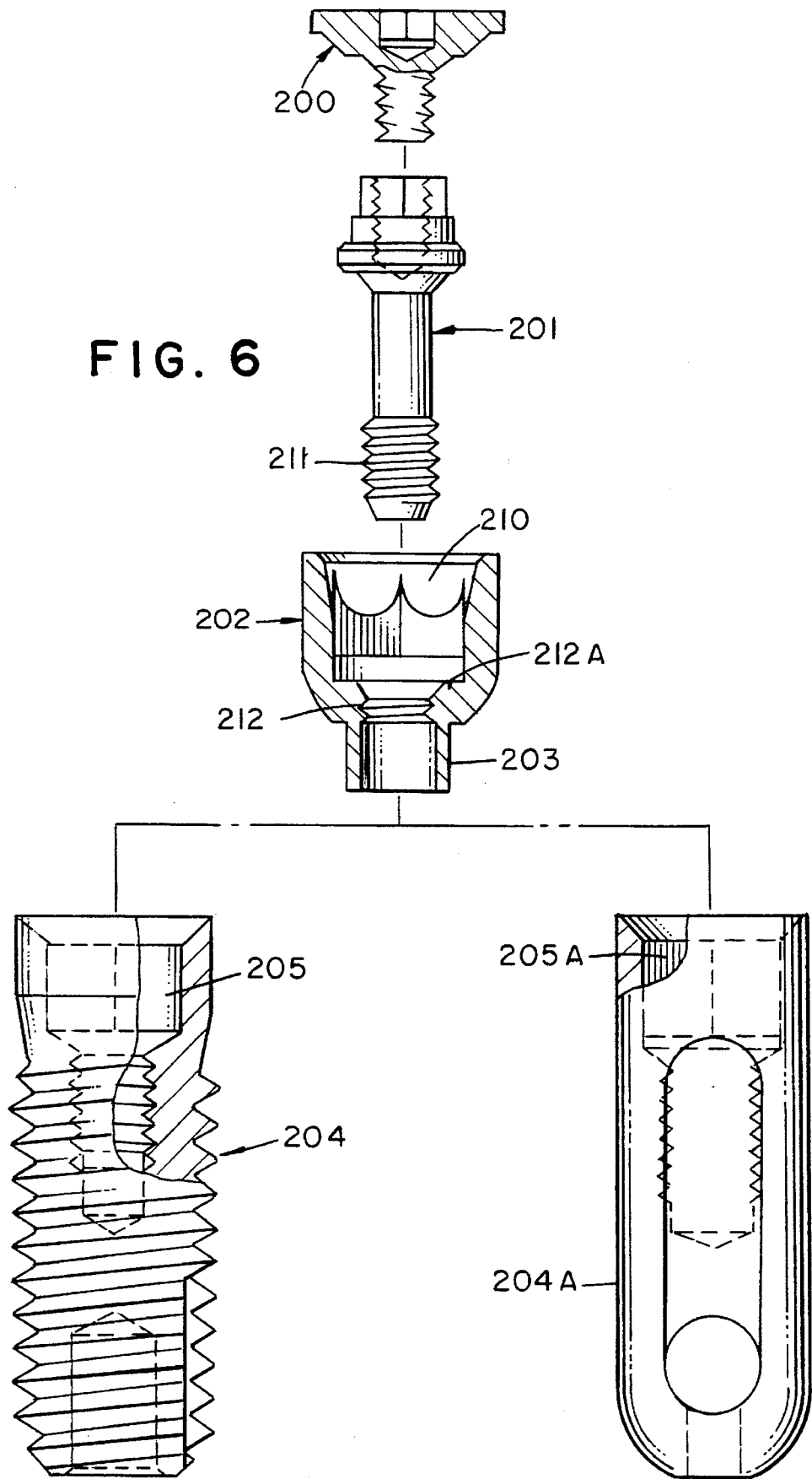
FIG. 6 shows another embodiment of a healing collar/fixation screw member/cover screw, here, a healing collar having a multi-sided male projection at one end that fits, frictionally or non-frictionally, into an internal, multi-sided passage inside an externally-threaded, or a non-externally threaded, cylindrical endosseous dental implant.

FIG. 1 shows an externally-threaded endosseous dental implant 1. Implant body 2 has external threads, and, at one end, an apical hole leading to internal passage 3. At the other end of implant 1, body 2 tapers outwardly into a cylindrical portion. Atop these tapered and cylindrical, unthreaded portions is a six-sided, male projection 4 having, at its center, opening 5 leading to internally-threaded passage 24 inside body 2.

Healing collar 6 has, at one end, opening 8, leading to an internal cavity having a plurality of untapered internal sides inside opening 8. Opening 8 fits over projection 4, frictionally or non-frictionally, and flat annular-shaped surface 25 seats on annular surface 27 surrounding projection 4 atop implant 1. Opening 7 at the other end of healing collar 6 also leads to an internal cavity having a plurality of untapered sides adapted to engage a tool such as an Allen wrench. Inside healing collar 6 are inwardly-projecting flange surface 26 and inwardly-projecting lower flange surface 27A.

Fixation screw member 13 includes threaded shank 16 that has a length and a screw pitch appropriate to engage the internal threads in passage 24 inside endosseous dental implant 1. Screw member 13 also includes unthreaded transition region 28 atop threaded shank 16, flange member 15 atop transition region 28, and hex-shaped projection 14 atop flange 15. Shank 16 of fixation screw 13 passes through internal passage 29 in healing collar 6, and engages the threads in internal passage 24 inside the body of the implant 1. When shank 16 is screwed into internal passage 24, the bottom surface of flange 15 engages flange surface 26 inside healing collar 6, and holds healing collar 6 onto implant 1.

Where healing collar 6 fits frictionally atop implant 1, threaded region 12 inside healing collar 6 permits disengagement of healing collar 6 from implant 1 by insertion of removal tool 100, shown in FIG. 3. Tool 100 has an internal, multi-sided passage 101 and a threaded distal region 102. Distal region 102 engages internal threads 12 inside healing collar 6, and, upon rotation of threads 12, disengages healing collar 6 from implant 1.

FIG. 1 also shows cover screw 17 that includes threaded shank 18, head member 19 and internal multi-sided passage 20 substantially centered atop head member 19. Passage 20 receives a tool such as a wrench to facilitate screwing cover screw 17 into healing collar 6. Either threads 12 or threads in passage 24 inside implant 1 can engage threaded shank 18.

FIG. 2 shows implant 1 affixed to healing collar 6 by fixation screw member 13. The implant 1/collar 6/fixation screw 13 assembly fits frictionally into cavity 30 at the bottom of stopper 38. Stopper 13 is preferably made of thermoplastic or thermosetting resin, and has a body portion 31 including annular notch 32. Cavity 34 at the top of stopper 38 has a tapering bottom region 35 that frictionally receives head member 19 of cover screw 17. Stopper 38 fits frictionally into an opening at the top of cylindrical vial 22. In turn, vial 22 fits inside cylindrical container 21. Atop container 21 is cover 36. Upon removal of cover 36 and withdrawal of vial 22 from container 21, stopper 38 can be removed from container 22, and used to carry implant 1/healing collar 6/fixation screw 13 to the jawbone of a patient. There, implant 1, with its attached healing collar 6 and fixation screw member 13, can be removed as a unit from stopper 38. Cover screw member 17 can thereafter be removed from cavity 34 for subsequent use.

FIGS. 4A and 4B show alternative embodiments of healing collar 6 and fixation screw 13. FIG. 4A shows fixation screw member 40 that includes elongated, threaded shank 41 having a size and shape appropriate to fit into internal passage 24 in implant 1. Atop threaded shank 41 is cylindrical, unthreaded portion 42, flange member 43, and hex-shaped projection 44. As FIG. 4B shows, healing collar 45 with its chamfered internal surface 46 and its tapered internal opening 47, receives fixation screw 40 with flange member 43 frictionally fitting against the internal walls 46 and the bottom of flange 43 seating on flange member 46 inside healing collar 45.

FIGS. 5A and 5B show a third healing collar embodiment, here generally designated 50, and a third fixation screw embodiment 52. Healing collar 50 has an opening 51 leading to an internal passage having an annular, downwardly and inwardly tapering wall, and a flange having annular flange surface 51A. Fixation screw 52 includes threaded shank portion 53 of dimensions appropriate to engage threads inside internal passage 24 of implant 1. Atop threaded shank 53 is cylindrical portion 54, flange member 55 and tool-engaging projection 56. Flange member 55 includes conical region 57 that seats inside healing collar 50 on internal wall surface 51. Flange 55 projects above healing collar 50, and can form part of an abutment for attachment to a dental prosthesis.

FIG. 6 shows another embodiment of a new healing collar, here generally designated 202. This healing collar 202 is substantially similar to the healing collar shown in FIGS. 1 and 2, except that, at the bottom end, healing collar 202 includes multi-sided, male projection 203. This multi-sided projection fits into a multi-sided, internal passage inside externally-threaded dental implant 204 or non-externally-threaded dental implant 204A. Projection 203 includes an internal passage that is collinear with the internal passage in the first cavity 210 at the top of healing collar 202, so that fixation screw 201 can pass through healing collar 202, and, by means of threaded shank 211, engage the threads in the internal passage 205 inside implant 204, or in internal passage 205A inside implant 204A. Cover screw 200 is substantially identical to cover screw 17 shown in FIG. 1, and is adapted to thread into an internally-threaded passage atop fixation screw 201 is adapted to thread into a threaded region 212 formed at the edge of the inwardly-projecting flange 212A inside healing collar 202.

Figure 7:
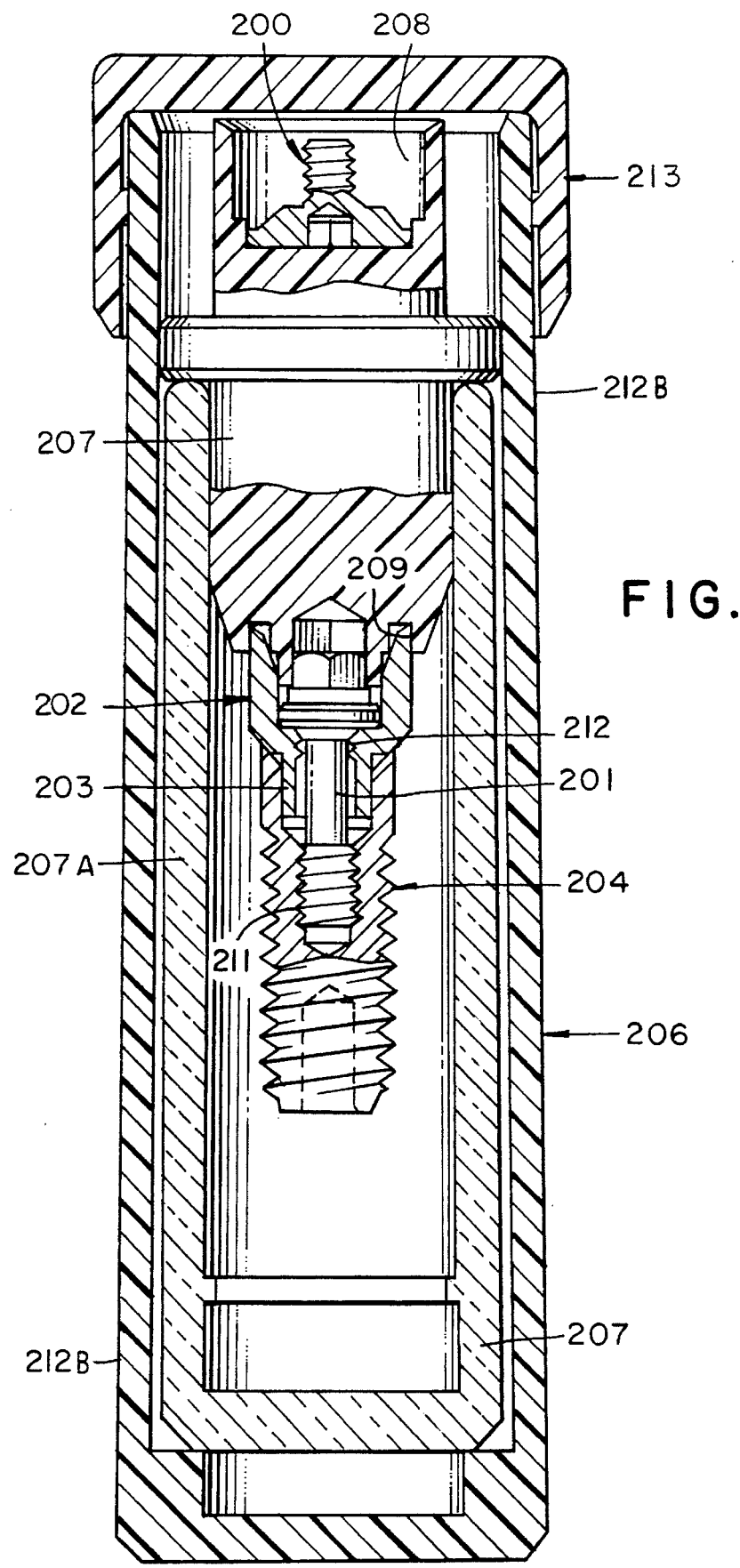
FIG. 7 shows a stopper and double-vial container for the healing collar/fixation screw/healing screw/implant shown in FIG. 6.

FIG. 7 shows a dental implant package 206 that is substantially the same as the package shown in FIG. 2. Here, stopper 207 has a first internal cavity 209 that receives and engages frictionally the outer surfaces of healing collar 202. Healing collar 202 is joined, by means of fixation screw 201, to implant 204 inside the package shown in FIG. 7. At the other end of stopper 207 is cavity 208, which frictionally engages cover screw 200. Like the package shown in FIG. 2, this package includes an outer vial 212B, an inner vial 207A, and cover 213 for outer vial 212B.

FIG. 8 shows an endosseous dental implant generally denoted 300 having threads 301 on its external body surface and an internal body cavity 302 having a beveled region 303 leading into a multi-sided cavity 304. Healing collar 305 includes multi-sided projection 306 at one end that has a size and shape complementary to the multi-sided internal cavity 304 of dental implant 300. Projection 306 seats itself in multi-sided cavity 304 with tapered region 307 of collar 305 seated against tapered internal surface 303 of implant 300.

FIG. 8 also shows a plurality of abutment screws suitable for use with dental implant 300 and healing collar 305. Abutment screw 308 includes threaded shank 309 with threads 318 at the bottom of shank 309. Abutment screw 308 has a beveled, inwardly-tapering region 311 that seats in the beveled internal surface 312 at the top of healing collar 305 when shank 309 is passed through healing collar 305 and screwed into internal threads 313 in dental implant 300. Abutment screw 308 also includes inwardly-tapering upper region 314 that has an internal passage 316 to receive a tool or a screw for attaching a prosthesis to the abutment. Abutment 316A also includes a threaded shank 317 with threads 318 at the bottom of threaded shank 317. This abutment screw has an inwardly-tapering, rounded, beveled portion 319 that seats on surface 312 of collar 305, internal passage 320 and multi-sided projection 321 for engaging an insertion tool. Abutment screw 322 includes threaded shank 323 having threaded portion 324 at the bottom. Abutment screw 322 includes inwardly-tapering rounded beveled portion 325 that seats on surface 312 of healing collar 305, and above beveled region 325, flange 326 and ball connector 327. Internal to ball connector 327 is multi-sided passage 328 that receives a tool for screwing abutment screw 322 into implant 300.

Figure 9D:
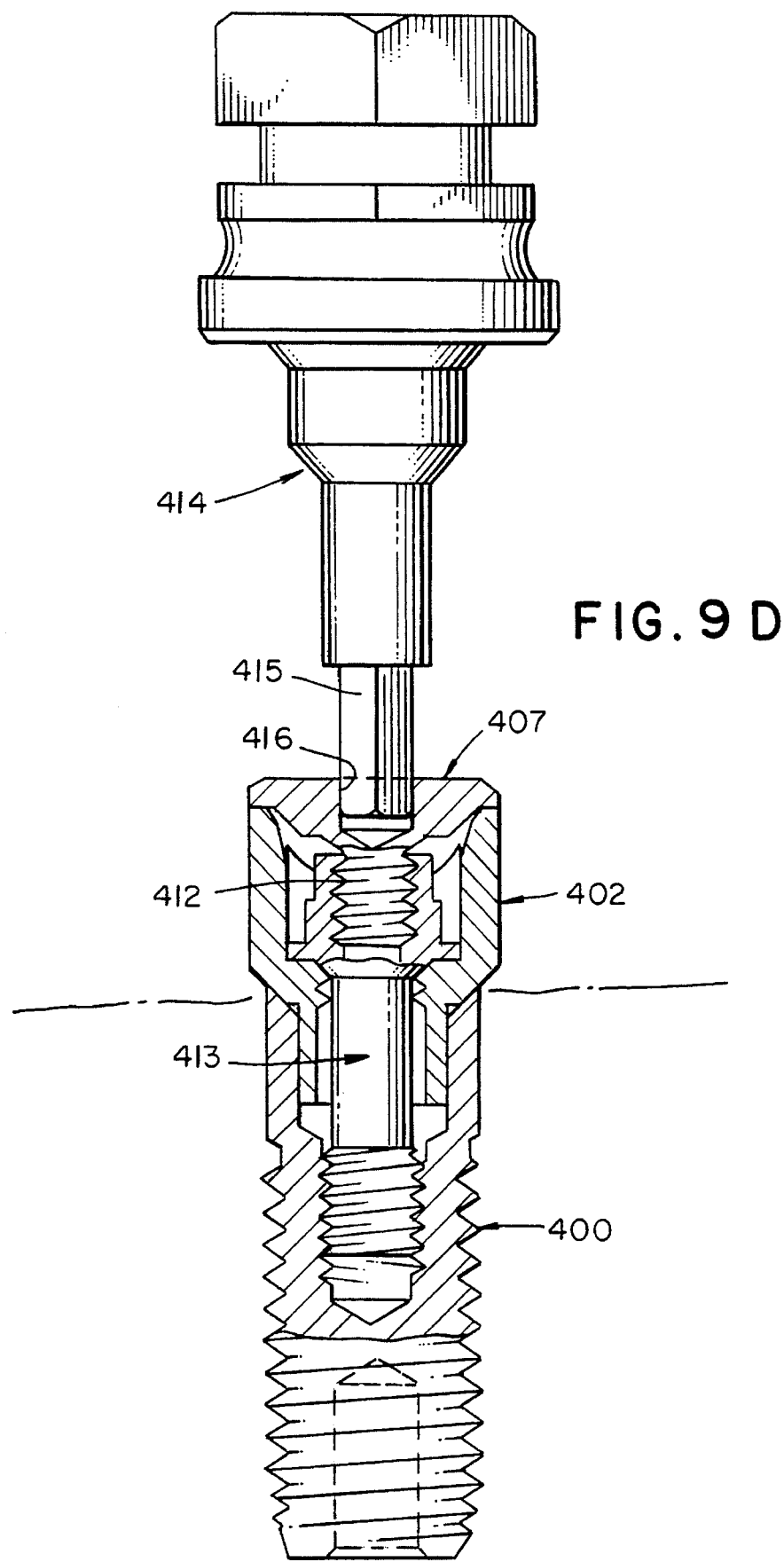
FIG. 9 shows, in view A, an embodiment of the stopper of this invention that engages both the internal and external walls of the healing collar of this invention; in view B, a tool that engages the healing collar of this invention with an abutment screw holding the healing collar to an endosseous dental implant; in views C, E, F and G, the use of the stopper of this invention to deliver a healing screw to an endosseous dental implant/healing collar combination; and in view D, these are the tools to fully seat a healing screw in place over a healing collar/implant combination.

FIG. 9 shows, in view A, endosseous dental implant 400 having an internal, multi-sided passage 403 and, seated in that internal passage at the top of implant 400, healing collar 402. Stopper 401 includes projection 404 that fits inside healing collar 402 at the top as seen in detail E and engages the internal walls of healing collar 402. Stopper 401 also has annulus 405 that engages healing collar 402 at its top edge as better seen in detail E. Stopper 401 also includes internal cavity 406 that frictionally engages healing screw 407. Stopper 401 includes annular projection 408 for engaging a tool suitable for manipulating stopper 401 as desired.

FIG. 9, in view B, also shows implant 400 joined to healing collar 402. View B shows tool 409 with external healing collar engagement means 410 and internal healing collar engagement means 411, which engage healing collar 402 externally and internally, respectively, as detail F shows.

FIG. 9, in views C, E, F and G, shows how stopper 401 is used to deliver healing screw 407 into an opening 412 in the top of abutment screw 413 inside endosseous dental implant 400. Detail G provides an assembled view of healing screw 407 delivered into the opening 412 while still attached to stopper 401.

FIG. 9, in view D, shows the use of screwdriver 414 with multi-sided shank 415 to screw healing screw 407 completely into the opening at the top of abutment screw 413 upon engagement of shank 415 with internal, multi-sided cavity 416 at the top of healing screw 407.

What is claimed is:

1. A healing collar joined to, and seated on an endosseous dental implant, said implant having an internal, threaded passage, and an external, multi-sided projection around the opening to said passage at the top of said implant, said implant being adapted for insertion with said collar into an opening in the jawbone of a person, said collar including:

a cylindrical-shaped external surface of a size and shape sufficient to form an opening in the mucosal tissue atop a passage formed in the jawbone of a patient to receive said implant;

a first cavity at one end of said healing collar, said cavity having the same number of sides as said projection atop said implant, and having a size and shape adapted to fit over said multi-sided projection atop said implant;

at the other end of said healing collar, an opening leading to a second, internal cavity having a plurality of sides, said internal cavity being adapted to engage a tool suitable for inserting said implant into said passage between said first and said second cavities, and inside said collar, an inwardly-projecting flange having an upper surface for engaging the head of a screw, and a lower surface for seating on the top of said implant; and a screw member that includes a head member joined to a threaded shank that has a size and shape sufficient to pass through said healing collar and engage the threads in said internal, threaded passage inside said implant, with said head member seating itself on said upper annular flange surface, leaving sufficient space for insertion of said tool into said cavity.

2. The healing collar product of claim 1 further comprising a cover screw including a threaded shank member joined to a head member, said head member including a tool-engaging surface for inserting said cover screw into the internal threads in the head of the fixation screw member, where the head of said fixation screw member includes such internal threads, or into said threaded internal passage in said implant, sealing the top of the healing collar.

3. The healing collar product of claim 2 wherein said cavity at said one end of said healing collar fits frictionally over said projection atop said implant.

4. The healing collar product of claim 1 wherein said cavity at said one end of said healing collar fits frictionally over said projection atop said implant.

5. A package comprising a vial and a packaging stopper of a size and shape appropriate to fit into an opening at one end of said vial for an endosseous dental implant, and inside said vial, said endosseous dental implant, said and a healing collar joined to, and atop said implant, implant having an internal, threaded passage, and an external, multi-sided projection around the opening to said passage at the top of said implant, said healing collar including a cylindrical-shaped external surface of a size and shape sufficient to form an opening in the mucosal tissue atop a passage formed in the jawbone of a patient to receive said implant;

a first cavity at one end of said healing collar having the same number of sides as said projection atop said implant, and having a size and shape adapted to fit over said projection atop said implant;

at the other end of said healing collar, an opening leading to a second, internal cavity having a plurality of sides, said internal cavity being adapted to engage a tool suitable for inserting said implant into said passage;

between said first and said second cavities, and inside said collar, an inwardly-projecting flange having an upper surface for engaging the head of a screw, and a lower surface for seating on the top of said implant; and a fixation screw member that includes a head member joined to a threaded shank that has a size and shape sufficient to pass through said healing collar, with said head member seating itself on said upper annular flange surface, leaving sufficient space in said internal cavity for insertion of said tool into said cavity;

said stopper including a plastic body having a size and shape appropriate to fit into an opening at one end of a vial for said endosseous dental implant;

at one end of said plastic body, a first internal cavity having a size and shape adapted to engage frictionally at least one member selected from the group consisting of the external walls of said healing collar and the multi-sided internal cavity at one end of said collar; and at the other end of said stopper, a second internal cavity having a size and shape adapted to receive and engage frictionally a cover screw, for use with said endosseous dental implant and said healing collar.

6. The package of claim 5 wherein the cavity at said one end of said healing collar fits frictionally over said projection atop said implant.

7. A healing collar joined to, and seated on an endosseous dental implant and adapted for insertion with said collar into an opening in the jawbone of a patient, said implant having an internal threaded passage and an internal, multi-sided cavity above the threads in said passage, said collar including:

a cylindrical-shaped, external surface of a size and shape sufficient to form an opening in the mucosal tissue atop a passage formed in the jawbone of a patient to receive said implant;;

at one end of said healing collar, a multi-sided projection having the same number of sides as the internal, multi-sided cavity inside said implant, said projection having a size and shape adapted to fit into said internal, multi-sided cavity in said implant;

at the other end of said healing collar, an opening leading to an internal cavity having a plurality of internal sides, said internal cavity being adapted to engage a tool suitable for inserting said implant into a passage formed in the jawbone of a patient to receive said implant;

at the base of said internal cavity in said healing collar, an inwardly-projecting flange having an upper surface for engaging the head of a screw, and a lower surface for seating on the top of said implant; and a fixation screw member that includes a head member joined to a threaded shank that has a size and shape sufficient to pass through said healing collar, with said head seating itself on said upper annular flange surface, leaving sufficient space in said internal cavity for insertion of said tool.

8. The healing collar of claim 7 further comprising a cover screw including a threaded shank member joined to a head member, said head member including a tool-engaging surface for inserting said cover screw into the internal threads in the head of said fixation screw member, where the head of said fixation screw member includes such internal threads, or into said threaded internal passage in said implant, sealing the top of the healing collar.

9. The healing collar of claim 8 wherein the multi-sided projection at said one end of said healing collar has a size and shape adapted to fit frictionally into said internal multi-sided cavity in said implant.

10. The healing collar of claim 8 wherein the multi-sided projection at said one end of said healing collar has a size and shape adapted to fit frictionally into said internal multi-sided cavity in said implant.

11. The healing collar product of claim 1 or claim 7 wherein said fixation screw member is an abutment screw having a threaded shank of a size and shape appropriate to pass through said healing collar and to engage internal threads inside said endosseous dental implant and a head portion that can support or retain a prosthesis by cement or threads, said head portion being connected to said threaded shank, said head portion having, near the connection to said threaded shank, a tapered region that mates and that interfits with a complementary region inside said cavity at said one end of said healing collar.

12. The healing collar product of claim 1 or claim 7 further comprising, inside said opening at said other end of said healing collar, and above said plurality of sides, a beveled, inwardly-tapering region having a size and shape suitable for receiving the head of an abutment screw having a complementary beveled surface.

13. The healing collar of claim 7 wherein the multi-sided projection at said one end of said healing collar has a size and shape adapted to fit frictionally into said internal multi-sided cavity in said implant.

14. The healing collar of claim 7 wherein the multi-sided projection at said one end of said healing collar has a size and shape adapted to fit frictionally into said internal multi-sided cavity in said implant.

15. A package comprising a vial and a packaging stopper of a size and shape appropriate to fit into an opening at one end of said vial and, inside said vial and attached to said stopper, an endosseous dental implant having, at its proximal end, an internal, multi-sided cavity and a healing collar, said healing collar including a cylindrical-shaped, external surface of a size and shape sufficient to form an opening in the mucosal tissue atop a passage formed in the Jawbone of a patient to receives aid implant;

at one end of said healing collar, a multi-sided projection having the same number of sides as the internal, multi-sided cavity inside said implant, said projection having a size and shape adapted to fit into said internal, multi-sided cavity in said implant;

at the other end of said healing collar, an opening leading to an internal cavity having a plurality of internal sides, said internal cavity being adapted to engage a tool suitable for inserting aid implant into a passage formed in the jawbone of a patient to receive said implant;

at the base of said internal cavity in said healing collar, an inwardly-projecting flange having an upper surface for engaging the head of a screw, and a lower surface for seating on the top of said implant; and a fixation screw member that includes a head member joined to a threaded shank that has a size and shape sufficient to pass through said healing collar, with said head seating itself on said upper annular flange surface, leaving sufficient space in said internal cavity for insertion of said tool, said stopper comprising:

a plastic body of a size and shape appropriate to fit into an opening at one end of a vial for said endosseous dental implant;

at one end of said body, a first internal cavity having a size and shape adapted to engage frictionally at least one member selected from the group consisting of the external walls of said healing collar and the multi-sided internal cavity at said one end of said collar; and at the other end of said stopper, a second internal cavity having a size and shape adapted to receive and engage frictionally a cover screw for use with said endosseous dental implant.

* * * * *